United States Patent

Marion et al.

[11] 4,000,177
[45] Dec. 28, 1976

[54] CATALYSTS AND PROCESSES FOR THE PREPARATION OF UNSATURATED NITRILES

[75] Inventors: Jacques Marion; Christian Pralus, both of Lyon, France

[73] Assignee: Produits Chimiques Ugine Kuhlmann, Paris, France

[22] Filed: Mar. 25, 1975

[21] Appl. No.: 561,698

[30] Foreign Application Priority Data

Mar. 28, 1974 France .......................... 74.10753

[52] U.S. Cl. .......................... 260/465.3; 252/456; 252/469
[51] Int. Cl.² ........................ C07C 120/14
[58] Field of Search .................. 260/469.3, 465.3

[56] References Cited

UNITED STATES PATENTS

| | | | |
|---|---|---|---|
| 3,152,170 | 10/1964 | Barclay et al. | 260/465.3 |
| 3,340,291 | 9/1967 | Barclay et al. | 260/465.3 |
| 3,471,545 | 10/1969 | Giordano et al. | 60/465.3 |
| 3,625,867 | 12/1971 | Yoshino et al. | 260/465.3 X |
| 3,681,421 | 8/1972 | Barclay et al. | 260/465.3 |
| 3,847,965 | 11/1974 | Gasson et al. | 60/465.3 |
| 3,879,435 | 4/1975 | Gasson et al. | 260/465.3 |
| 3,914,278 | 10/1975 | Gasson et al. | 260/465.3 |

*Primary Examiner*—Joseph Paul Brust
*Attorney, Agent, or Firm*—Brooks Haidt Haffner & Delahunty

[57] ABSTRACT

Catalysts for the preparation of unsaturated nitriles by the ammoxidation of olefins, the catalysts comprising oxides of antimony, tin, tungsten, and copper having the general formula $$Sb_a Sn_b W_c Cu_d O_e \qquad (I)$$

wherein $a$ is from one to ten, $b$ is from one to ten, $c$ is from 0.01 to 5, $d$ is from 0.01 to 5, and $e$ is the number of oxygen atoms in combination with the metallic elements of formula (I), together with processes for preparing unsaturated nitriles by olefin ammoxidation, and particularly for preparing acrylonitrile from propylene, utilizing such catalysts.

4 Claims, No Drawings

CATALYSTS AND PROCESSES FOR THE PREPARATION OF UNSATURATED NITRILES

BACKGROUND OF THE INVENTION

This invention relates to the preparation of unsaturated nitriles from olefins, and more particularly to the vapor phase ammoxidation of propylene or isobutene, respectively, to acrylonitrile or methacrylonitrile in the presence of catalysts based on the combination of antimony, tin, copper, and tungsten.

It is known in the art, particularly from French Pat. Nos. 1,299,139 and 1,293,088, that catalysts based on the oxides of antimony and the oxides of tin permit production of unsaturated nitriles from olefins. It has been stated in other patents, particularly in Certificate of Addition 81,246 to French Pat. No. 1,299,139 and in French Pat. Nos. 2,176,770 and 2,176,771, that the oxides of polyvalent metals such as iron, copper, vanadium, titanium, calcium and barium can be advantageously used with the oxides of antimony and of tin to oxidize propylene to acrylonitrile in the presence of ammonia.

Other combinations of oxides of polyvalent metals with oxides of antimony and of tin have been shown in a very general manner in various patents as French Pat. Nos. 2,020,512 and 2,065,317, and British Pat. No. 1,280,073. Certain of these combinations, in particular those shown in French Pat. No. 2,176,771, provide a high rate of conversion of propylene to acrylonitrile, but they necessitate relatively lengthy contact times which result in insufficient productivity for industrial needs.

THE INVENTION

It has unexpectedly been found according to the present invention that a particularly valuable catalyst formulation can be prepared for the ammoxidation of olefins to unsaturated nitriles, and particularly for the conversion of propylene to acrylonitrile, when a combination of the oxides of antimony, tin, tungsten, and copper are used, to the exclusion of other added metallic oxides, as further described herein.

The catalysts of this invention are represented by the empirical formula

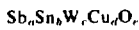   (I)

$Sb_a Sn_b W_c Cu_d O_e$ wherein $a$, $b$, $c$, and $d$ represent numbers and have the following values: $a$ is from 1 to 10, $b$ is from 1 to 10, $c$ is from 0.01 to 5, $d$ is from 0.01 to 5, and the number of atoms of oxygen represented by $e$ in the combination is that obtained by combining the metallic elements of formula (I). This number, represented by $e$, depends upon the particular compound or compounds obtained among the metallic elements during the preparation of the catalyst. It is not generally critical in the practice of this invention and $e$ generally ranges from about 4 to about 65.

These catalysts are particularly suited to ammoxidation processes for converting olefins, preferably lower olefins, to corresponding nitriles. Such ammoxidation processes are carried out using a feed stream of olefin, oxygen-containing gas, and ammonia with the novel catalysts herein described.

All the catalysts which respond to the ratios defined in empirical formula (I) have a high activity for the preparation of acrylonitrile, but it has been discovered according to the present invention that the best results are generally obtained when the elements antimony, tin, tungsten, and copper are combined in such a fashion that the numbers $a$, $b$, $c$, and $d$ of formula (I) have the following relative values: $a$ is from about 2 to about 5, $b$ is from about 1 to about 3, $c$ is from about 0.1 to about 1, and $d$ is from about 0.1 to about 1.

The catalysts according to the present invention can be prepared in a number of ways. For example, they can be made by intimately mixing the oxides, by separate precipitation or by coprecipitation starting with salts or soluble compounds of the constituent elements, by separate or simultaneous thermal decomposition of compounds convertible to oxides by heating, or by a combination of such techniques.

Regardless of the method utilized to prepare the catalysts, they are subsequently subjected to a thermal treatment at temperatures between about 500° C and 1000° C under an oxygen-containing atmosphere, for example, air. In certain embodiments, temperatures in the range of from about 700° C to 900° C are preferred.

A preferred method for preparing catalysts having the formula according to the present invention comprises dispersing antimony oxide in an aqueous solution of nitric acid, adding powdered metallic tin into the suspension of antimony trioxide, using heat and agitation to convert the tin to oxide, eliminating the residual nitric acid by successive decantation, siphoning, and washing with cold and hot water, adding copper in the form of cupric nitrate and tungsten in the form of its trioxide to the mixture of the oxides of antimony and tin, precipitating the copper in the form of hydroxide with ammonia, separating the precipitate by filtration after decantation, and finally drying the precipitate and putting it into an appropriate form, such as pellets, before heat treatment under a stream of air.

After the thermal treatment, the catalysts of formula (I) according to the present invention are ready for use. They have shown themselves to be particularly useful for catalyzing ammoxidation reactions of olefins, and in particular propylene, under the usual well-known operating conditions. In the case of the ammoxidation of propylene, the reactants used are oxygen, ammonia, and the propylene which can be admixed with paraffinic hydrocarbons such as those which are present in commercial propylene, that is to say, ethane and propane, among other hydrocarbons. Air is customarily used as the source of oxygen for reasons of economy.

The molar ratio of oxygen to propylene and of ammonia to propylene can be varied over a wide range of values. The molar ratio of oxygen to propylene is generally from about 0.5/1 to 3/1, and in the present process is preferably greater than about 1.5/1. The molar ratio of ammonia to propylene is generally from about 0.7 to about 3 and in the present process is preferably from about 0.9 to about 1.5

The catalytic conversion of propylene to acrylonitrile is desirably conducted in the presence of water vapor or of an inert diluent which can comprise from about 5 to about 40% of the volume and is most generally from about 10 to about 25% of the total volume of reactants.

The temperature of the reaction stabilizes between about 350° and 520° C and is most generally between 380° and 500° C. The pressure which is utilized in the reaction can be subatmospheric or superatmospheric and is most preferably atmospheric pressure.

The contact times calculated for normal temperature and pressure, that is, at 0° C and 760 mm Hg, can vary widely. For example, contact times of from about 0.5 to about 10 seconds can be used, and contact times of from about 1 to about 6 seconds are normally used. Some particularly advantageous results are obtained with a contact time of from about 2 to about 4 seconds, and this meets the requirements of industrial use.

The catalyst can be used in the ammoxidation process in a variety of forms such as pellets, extruded rods, grains, or fine particles and the like according to the type of reactor in which the catalyst is to be utilized. More particularly, the form used is chosen according to whether the catalysts are used in fixed beds or in fluidized beds. A particularly preferred form is short rods. The catalyst can be used as-is, solely comprised of mixtures of the prepared oxides or it can be deposited in an appropriate fashion according to known processes on a catalyst support or carrier of the classical type, such as silica and like materials.

All parts, percentages, proportions, and ratios herein are by weight, unless otherwise indicated.

The following examples are given to illustrate embodiments of the invention as it is presently preferred to practice it. It will be understood that these examples are illustrative, and the invention is not to be considered as restricted thereto except as indicated in the appended claims.

EXAMPLE I

An aqueous solution of 2065 g of nitric acid containing 18.5% of $HNO_3$ is heated under agitation at 95° C, and 438 grams of antimony oxide, $Sb_2O_3$, in powder form, is dispersed in the solution. Then 90 g of tin in powder form is added while the temperature of the solution is maintained at 97° to 99° C.

The suspension is thereafter maintained at boiling for 15 minutes and then, with continuous agitation, cooled to 40° C. The agitation is stopped, and after decantation, the supernatant liquid is removed by siphoning. The remaining mass is then washed under agitation for 15 minutes; first with 4 liters of cold water and then after decantation and siphonage of the supernatant liquid, it is again washed with 4 liters of water at 90° to 100° C.

After cooling to 40° C, siphonage, and decantation of the supernatant liquid, the solids are again suspended in 2.5 liters of water and maintained at 60° C. Then, 43.5 g of tungsten anhydride, $WO_3$, and 181.2 g of cupric nitrate, $Cu(NO_3)_2 \cdot 3H_2O$ is then added. Ammonia is then introduced into the liquid until a pH of 6.3 to 6.5 is obtained. After cooling, decantation, and siphonage of the supernatant liquid, the mass is washed under agitation with 4 liters of cold water for 10 minutes and is then separated by filtration, dried for 12 hours at 150° C, and pelletized after the addition of 1% graphite as a lubricant. The pellets so obtained are then heat-treated under a stream of air for 16 hours at 800° C.

The catalyst so prepared is in the form of 2.5 to 4 mm granules, and the metallic elements are in the atomic ratio Sb/Sn/W/Cu of 4/1/0.25/1. Thirty milliliters of these pellet particles are placed in a catalytic reactor comprising a glass U-tube having a 10 mm inside diameter. This reactor is immersed in a molten nitrate salt bath at 490° C, and 18 liters/hr of gaseous mixture having a molar composition of 5.7% propylene, 0.3% propane, 6% ammonia, 65% air, and 23% water vapor is introduced to provide a contact time of 6 seconds.

The rate of conversion of propylene to acrylonitrile is 73.4%; to hydrogen cyanide, 5.0%; to acrolein, 2.1%; to $CO_2$, 10.7%; to CO, 4.5%; and 4.3% of the propylene is unreacted.

EXAMPLE II

A catalyst is prepared according to the procedure of Example I but in the form of cylindrical pellets having dimensions of 4×5 mm and with a Sb/Sn/W/Cu ratio of 4/3/0.25/0.5, and 30 ml of this catalyst material is charged into the same reactor as used in Example I. The temperature of the molten nitrate bath is maintained at 470° C. Into this reactor is introduced 43.5 liters/hr of a gaseous mixture containing molecular proportions of 6% propylene, 7% ammonia, 70% air, and 17% water vapor, which provides a contact time of 2.5 seconds.

Under these conditions, the rate of conversion of the propylene to acrylonitrile is 67.8%. Also obtained is 6.4% hydrogen cyanide, 1.5% acrolein, 8.9% $CO_2$, and 4.3% CO; and 9% of the propylene is unchanged.

EXAMPLE III

The same reactor as that utilized in Example I is charged with 30 ml of a catalyst having a Sb/Sn/W/Cu atomic ratio of 4/2/0.25/0.5 in the form of 4×5 mm pellets prepared as indicated in Example I and thermally treated at 750° C. There is then introduced into the reactor 27 liters/hr of a gaseous mixture containing, on a molar basis, 7% propylene, 8% ammonia, 70% air, and 15% water vapor, which corresponds to a contact time of 4 seconds.

Under these conditions the rate of conversion of propylene to acrylonitrile is 68.7%, and the product stream also contains 5.7% hydrogen cyanide, 0.9% acrolein, 10.2% $CO_2$, 4.2% CO, and 7.7% of unreacted propylene.

EXAMPLE IV

The catalyst of Example III is thermally treated at 800° C and is placed in a steel reactor, having a height of 3 meters and an inside diameter of 25 mm, and the reactor is submerged in a molten nitrate bath maintained at 460° C. A gaseous mixture containing, on a molar basis, 5.7% propylene, 0.3% propane, 7.0% ammonia, 70.0% air, and 17.0% water vapor is introduced into the reactor at the rate of 1480 liters/hr, which provides a contact time of 4 seconds.

The rate of conversion of propylene to acrylonitrile is 68.2%, and the product stream also contains 7.6% hydrogen cyanide, 0.7% acrolein, and 14.8% of carbon oxides.

EXAMPLE V

Under agitation, 225 g of an aqueous nitric acid solution containing 18.5% of $HNO_3$ is heated at 95° C, and 58.4 g of antimony oxide, $Sb_2O_3$, in powder form is dispersed into this solution, followed by 24 g of powdered tin, while the temperature is kept at 97°–99° C. The suspension is thereafter maintained for 15 minutes at boiling and then, with constant agitation, cooled to 40° C. The agitation is stopped and, after decantation, the supernatant liquid is removed by siphonage. The remaining slurry is then washed under agitation for 15 minutes with 4 liters of cold water, and then after decantation and siphonage of the supernatant liquid, again with 4 liters of water at 98°–100° C.

After cooling to 40° C and decantation and siphonage of the supernatant liquid, the slurry is resuspended in 2.5 liters of water and maintained at 60° C. Then 5.8 g of tungstic anhydride, $WO_3$, is added followed by 12 g of copper nitrate, $Cu(NO_3)_2 \cdot 3H_2O$. Ammonia is introduced until a pH of 6.3–6.5 is reached.

After cooling, decantation, and siphonage of the supernatant liquid, the solids are washed under agitation with 4 liters of cold water for 10 minutes, separated by filtration and then dried for 12 hours at 150° C. One hundred parts of the dry cake is mixed with 20 parts of water in a mixing machine for 30 minutes and the resulting paste is drawn through an extruder to obtain short rods or filaments which are 5 mm in diameter and 4 mm long. These rods are dried for 12 hours at 120° C and thermally treated for 16 hours under a stream of air at 775° C.

A catalytic reactor comprising a glass U-tube with an inside diameter of 10 mm is charged with 59 g of this catalyst. The reactor is immersed in a molten nitrate bath heated to 480° C, and a gas mixture containing, on a molar basis, 7% propylene, 0.5% ammonia, 74.5% air, and 10% water vapor is passed through the reactor at the rate of 30.8 liters/hr.

This process provides a 72.4% conversion of propylene to acrylonitrile, 5.8% hydrogen cyanide, 0.9% acrolein, 10.6% of carbon oxides, that is, carbon monoxide and carbon dioxide, and 10.3% of unreacted propylene.

EXAMPLE VI

Example I is repeated utilizing 59 g of the catalyst of Example I in the reactor. The bath temperature is maintained at 470° C, and 30.8 liters/hr of a mixture containing, on a molar basis, 6% propylene, 7% ammonia, 70% air, and 17% water vapor is introduced into the reactor.

Under these conditions, 74.3% of the propylene is converted to acrylonitrile, 0.9% to acrolein, 6.5% to hydrogen cyanide, and 12.9% to carbon oxides; and 5.4% of the propylene is unreacted.

EXAMPLE VII

A catalyst is prepared according to Example I except that the slurry of oxides of antimony and of tin is neutralized to a pH of 6.5 with ammonia after washing and before the steps of adding the tungsten oxide and cupric nitrate.

The catalyst in the form of 5 mm rods is heat-treated at 775° C, and 55.5 g is charged to the reactor of Example I. Operating at a molten salt bath temperature of 470° C with a feed gas mixture introduced at the rate of 30.8 liters/hr and having a molar composition of 6% propylene, 7% ammonia, 70% air, and 17% water vapor, a 73.2% conversion of propylene to acrylonitrile is obtained, with 0.4% of acrolein, 5.7% hydrogen cyanide, 15.6% of carbon oxides, and 5% of the propylene is unreacted.

It will be appreciated by those skilled in the art from the present description that the catalysts and processes are quite useful for conversion of lower olefins to the corresponding nitriles and that propylene and isobutene can readily be used to provide acrylonitrile and methacrylonitrile.

What is claimed is:

1. A process for producing acrylonitrile or methacrylonitrile which comprises reacting, respectively, propylene or butylene, ammonia, and oxygen in the presence of a catalyst consisting essentially of oxides of antimony, tin, tungsten, and copper according to the formula $$Sb_a\ Sn_b\ W_c\ Cu_d\ O_e$$

where $a$ is from 1 to 10, $b$ is from 1 to 10, $c$ is from 0.1 to 5, $d$ is from 0.1 to 5, and $e$ is the number of oxygen atoms in combination with the metallic elements, and is from 4 to 65, the catalyst being prepared by intimately mixing the oxides, by separate precipitation or coprecipitation starting with salts or soluble compounds of the elements, by separate or simultaneous thermal decomposition of compounds convertible to the oxides by heating, or a combination thereof and being subjected to a thermal treatment at temperatures between about 500° and 1000° C, to produce the corresponding nitrile.

2. A process according to claim 1 wherein $a$ is between 2 and 5, $b$ is between 1 and 3, $c$ is between 0.1 and 1, and $d$ is between 0.1 and 1.

3. A process according to claim 1 wherein the temperature is from 350° to 520° C and the contact time is from 0.5 to ten seconds.

4. A process according to claim 1 wherein the thermal treatment is carried out at 700° to 900° C.

* * * * *